United States Patent
Ohmer et al.

(10) Patent No.: US 10,172,552 B2
(45) Date of Patent: Jan. 8, 2019

(54) METHOD FOR DETERMINING AND ANALYZING MOVEMENT PATTERNS DURING DENTAL TREATMENT

(71) Applicant: Benjamin Ohmer

(72) Inventors: Benjamin Ohmer, Munich (DE); Stefan Raith, Mitterfels (DE)

(73) Assignee: Benjamin Ohmer, Munich (DE)

( * ) Notice: Subject to any disclaimer, the term of this patent is extended or adjusted under 35 U.S.C. 154(b) by 272 days.

(21) Appl. No.: 14/898,176

(22) PCT Filed: Jun. 11, 2014

(86) PCT No.: PCT/EP2014/062077
§ 371 (c)(1),
(2) Date: Dec. 14, 2015

(87) PCT Pub. No.: WO2014/202438
PCT Pub. Date: Dec. 24, 2014

(65) Prior Publication Data
US 2016/0235357 A1    Aug. 18, 2016

(30) Foreign Application Priority Data

Jun. 19, 2013 (DE) .......... 10 2013 010 292
Sep. 18, 2013 (DE) .......... 10 2013 015 537
Dec. 17, 2013 (DE) .......... 10 2013 021 492

(51) Int. Cl.
*G01P 21/00* (2006.01)
*A61B 5/00* (2006.01)
(Continued)

(52) U.S. Cl.
CPC .......... *A61B 5/486* (2013.01); *A46B 15/0006* (2013.01); *A46B 15/0012* (2013.01);
(Continued)

(58) Field of Classification Search
CPC ... A61C 17/221; A61C 17/22; A46B 15/0012; A46B 15/0006; A46B 2200/1066;
(Continued)

(56) References Cited

U.S. PATENT DOCUMENTS 6,536,068 B1 * 3/2003 Yang .................. A46B 15/0002
15/105
6,786,732 B2 * 9/2004 Savill ................. A46B 15/0002
434/263
(Continued)

FOREIGN PATENT DOCUMENTS

DE        10045067      4/2002
DE     102008027317    11/2011
(Continued)

*Primary Examiner* — An Do

(57) ABSTRACT

The invention refers to a method for the at least partial determination of a movement pattern of a dental treatment means, in particular tooth cleaning, resulting during a dental treatment and comprises at least the steps:
Moving the dental treatment means at least in a x-/y-plane for the treatment of surface parts of the teeth, wherein by means of an optical detection device data are recorded with respect to at least one motion parameter, in particular the movement direction or –rotation, the acceleration, the path and/or the velocity, of the dental treatment means with respect to a reference system moving with the head of the treated person and providing the recorded data to a processor device for the determination of the movement pattern.

17 Claims, 2 Drawing Sheets

Figure 1A:
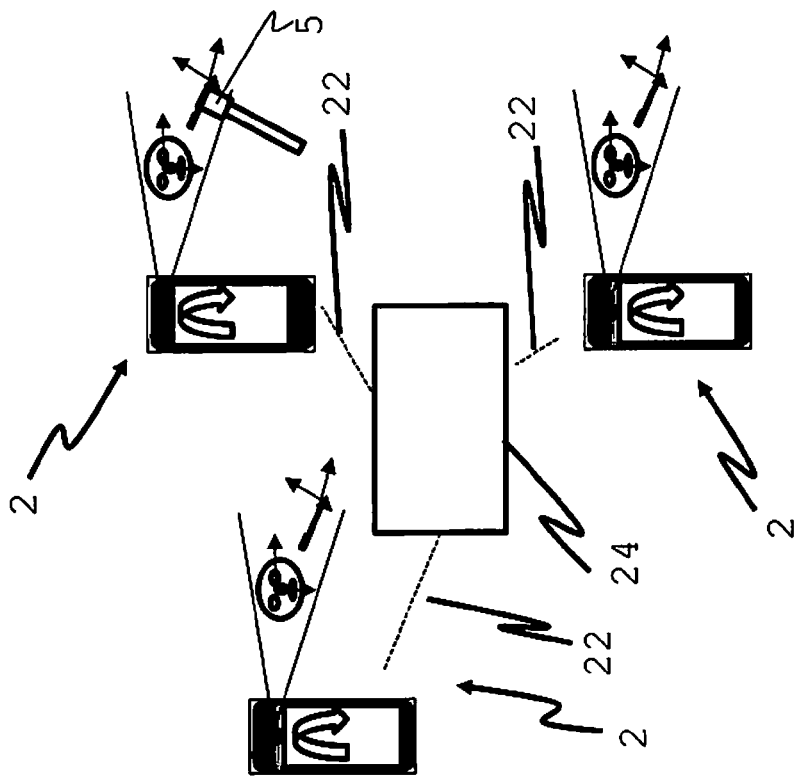

(51) Int. Cl.
*A46B 15/00* (2006.01)
*A61B 5/11* (2006.01)
*A61C 19/04* (2006.01)
*A61C 17/22* (2006.01)

(52) U.S. Cl.
CPC .......... *A61B 5/0077* (2013.01); *A61B 5/1123* (2013.01); *A61B 5/1128* (2013.01); *A61B 5/6898* (2013.01); *A61C 17/221* (2013.01); *A61C 19/04* (2013.01); *A46B 2200/1066* (2013.01); *A61B 5/4833* (2013.01); *A61C 17/22* (2013.01)

(58) Field of Classification Search
CPC ..... A61B 5/486; A61B 5/1123; A61B 5/1128; A61B 5/0077; A61B 5/4833; A61B 5/4547
USPC ............................................... 702/85, 94, 95
See application file for complete search history.

(56) References Cited

U.S. PATENT DOCUMENTS

| | | | |
|---|---|---|---|
| 7,748,089 B2 | 7/2010 | Jalbert et al. | |
| 9,498,053 B2* | 11/2016 | Patel | A46B 15/0006 |
| 9,642,685 B2* | 5/2017 | Brodkin | A61C 9/0053 |
| 9,724,001 B2* | 8/2017 | Dykes | A61B 5/02427 |
| 9,757,065 B1* | 9/2017 | Suri | A61B 5/4833 |
| 9,882,986 B2* | 1/2018 | Patel | G16H 10/00 |
| 9,901,256 B2* | 2/2018 | Seibel | G01N 21/645 |
| 9,907,463 B2* | 3/2018 | Elazar | A61B 1/247 |
| 9,918,013 B2* | 3/2018 | Ryan | H04N 5/23293 |
| 9,950,434 B2* | 4/2018 | Binder | H04N 13/194 |
| 2002/0183959 A1* | 12/2002 | Savill | A46B 15/0002 702/150 |
| 2008/0146887 A1 | 8/2008 | Rao et al. | |
| 2009/0215015 A1 | 8/2009 | Chu | |
| 2010/0170052 A1* | 7/2010 | Ortins | A46B 15/0002 15/106 |
| 2010/0281636 A1* | 11/2010 | Ortins | A46B 9/04 15/4 |
| 2010/0323337 A1* | 12/2010 | Ikkink | A46B 15/0002 434/263 |
| 2011/0131014 A1* | 6/2011 | Bates | G06T 17/10 703/1 |
| 2011/0247156 A1* | 10/2011 | Schmid | A46B 15/0002 15/105 |
| 2011/0275424 A1 | 11/2011 | Schmid et al. | |
| 2012/0251975 A1* | 10/2012 | Iwahori | A61C 17/3481 433/119 |
| 2012/0295218 A1* | 11/2012 | Moll | A61C 17/0211 433/32 |
| 2013/0323674 A1* | 12/2013 | Hakomori | A61B 5/0088 433/29 |
| 2014/0215370 A1* | 7/2014 | Berry | G06F 3/04845 715/769 |
| 2015/0381923 A1* | 12/2015 | Wickenkamp | H04N 5/783 386/344 |
| 2016/0143718 A1* | 5/2016 | Serval | A46B 15/0022 15/22.1 |
| 2016/0284208 A1* | 9/2016 | Pfenniger | A61C 17/224 |
| 2016/0296163 A1* | 10/2016 | Chaudhry | A46B 15/0004 |
| 2017/0079421 A1* | 3/2017 | Tamminga | A61C 1/0015 |

FOREIGN PATENT DOCUMENTS

| | | |
|---|---|---|
| DE | 102011103301 | 12/2012 |
| EP | 2189198 | 5/2010 |
| KR | 100760351 | 9/2007 |
| WO | 02083257 | 10/2002 |
| WO | 2006/137648 | 12/2006 |
| WO | 2011073010 | 6/2011 |

* cited by examiner

METHOD FOR DETERMINING AND ANALYZING MOVEMENT PATTERNS DURING DENTAL TREATMENT

The invention refers to a system and a method for determining of movement patterns during a dental treatment, in particular a teeth cleaning. Due to relatively large intervals of up to several month or even years between single dental visits the problem results, that the instructions of the dental surgeon with respects to frequency, duration and manner of the treatment are easily forgettable or over time motion sequences establish which are not optimal, whereby the oral hygiene is not optimally ensured or defects of the oral cavity, in particular of solid and/or soft oral parts, like e.g. the teeth, the jaw and/or the gum, are caused.

The printed publication EP 1 379 149 B1 discloses a method for monitoring of the position of a toothbrush with respect to the teeth of a person, wherein the method comprises: Providing a toothbrush having a first position sensor, wherein the first position sensor reacts at least sensible on changes of the position and orientation, providing a second position sensor in a fixed position with respect to the teeth, wherein the second position sensor reacts sensible on changes of the position and orientation; Transfer of the output of the first position sensor and the second position sensor to a processing apparatus, and the processing apparatus compares both sensor outputs for monitoring the position of the toothbrush during a period of time with respect to the teeth.

This system is disadvantageous, since expensive sensors must be attached to a face in a defined manner, whereby the system is costly and complex, whereby a high acceptance of the market is difficult.

Yu-Chen Chang et. al. describe in the article "Playful Toothbrush: UbiComp Technology for Teaching Tooth Brushing to Kindergarden Children" a system in which the movement of the toothbrush is optically detected. This system is disadvantageous, since the detected movements take place in an undefined manner in space, whereby a movement of the head causes a falsification of the detected data. Further expensive modifications of the toothbrush are required, whereby the system is complex and costly and thus a mass market seems to be inaccessible. Additionally the system has to be installed fixed in space, that a camera can detect the modified toothbrush in a defined manner.

Further, both systems are based on given data sets, whereby an enhancement of the knowledge with respect to tooth brushing movements is not possible.

It is therefore the object of the present invention to provide a method and a system, which enables an optimization of the oral health, in particular oral hygiene, tooth health, jaw health and/or gum health. Preferably, the invention shall also enable a control, in particular for continuous or permanent control, respectively a monitoring, in particular for continuous or permanent monitoring, of the oral hygiene. Further preferably, the invention shall be simple as possible, low-priced and usable by as many persons as possible.

This object is solved on the one hand side by a method according to claim 1.

The method according to the invention preferably comprises the step moving the dental treatment means at least in an X/Y plane in order to treat surface portions of the teeth, wherein data relating to at least one movement parameter, in particular the movement direction or rotation, the acceleration, the path and/or the speed, of the dental treatment means relative to a reference system which moves with the head of the treated person are recorded by means of at least one optical detection device, the step of defining a further three-dimensional reference system by means of a processor device, wherein the further reference system moves at least at times and preferably constantly during a movement of the dental treatment means in space with the dental treatment means, wherein the further reference system is formed by the characteristic body points of the hand, body lines of the hand and/or body surfaces of the hand by which the dental treatment means is being guided, the step of providing the recorded data to a processor device for determination of the movement pattern and the step of determining the movement pattern.

Preferably, the dental treatment means is moved at least at times three dimensionally, that means in X-, Y-, and Z-direction, and the movement parameters are particular preferably dependent on the direction and/or orientation recorded. The X-Y plane is a plane, which extends in X-direction and in Y-direction, possible other planes are extending in an analog manner, wherein the X-/Y-/Z-axis are orthogonal to each other.

Alternatively or additionally the present invention can refer to a method for at least partially determination of a, in particularly person focused, movement pattern of a dental treatment means, in particular a toothbrush, resulting from a dental treatment, in particular tooth cleaning, wherein the method preferably comprises at least the step of optical recording of data, in particular by means of at least one camera, with respect to at least one movement parameter, in particular the movement direction or rotation, the acceleration, the traveled path and/or the speed, of a dental treatment means and the step of a figurative separation of the dental treatment means, in particular of the hand guiding the dental treatment means, from at least one further image part recorded by means of the optical detection device and the step of determining at least one movement parameter corresponding to the movement pattern.

This solution is advantageous, since the data recording takes place independently of the place as well as time and thus a monitoring and objective judgement of the dental treatment can happen also at the home of private individuals at any time, that means independent from the time. The recorded data are processed in such a manner, in particular in real time, respectively are preferably processed in real time in such a manner, that the movement pattern is analyzable by e.g. an attending physician or a private individual respectively a patient, whereby individual adaptations of the movement patterns taking place during a dental treatment can take place. The data collected in such a manner cannot only be used for individually for acute optimization of the movement pattern, but can also be used in larger scalings e.g. of health insurance companies and/or research institutes. By means of transferring data to a central evaluation station it is made possible e.g. on the one hand side to provide a possibility to process the raw data centralized with adequate computing power, to compare it with optimal movement schematas and to send it to the local end-user devices, on the other hand it is additionally or alternatively possible to provide data for large clinical studies for research purposes or for commercial statistic usage (e.g. health insurance companies).

Further preferred embodiments, subject-matters, method steps and configurations are subject-matter of the dependent claims.

According to a further preferred embodiment of the present invention a method for determining at least one movement characteristic is provided The method preferably comprises at least the step of carrying out the method according to claim 1 multiple times, in particular on different end-user devices for recording of movement patterns of differing persons and preferably their statistic evaluation, wherein it is additionally or alternatively also conceivable that a movement characteristic is generated respectively determined for one person, and the step of determining at least one coinciding property, in particular a movement parameter and/or the dental treatment duration, of the determined movement patterns or the recorded data.

This embodiment is advantageous, since one or more movement characteristic are derivable from the movement pattern of individual persons, which are representative for the dental treatment behavior of the respective person. However it is additionally or alternatively conceivable that the movement pattern or movement characteristic of individual persons are grouped respectively become grouped due to matching features. Furthermore, it is conceivable that a step of correlating the determined movement patterns or of the recorded data with characterizing standard data takes place, wherein those are provided in a database, wherein the database is at least partially provided locally on a mobile end-user device and/or at least partially on a server.

Further it is conceivable that during an usage of the device a step of outputting, in particular optical, haptic and/or acoustic outputting, for informing about correction-, standard- and/or ideal-movements, in particular in dependency of the actual, that means e.g. in real time, determined movement patterns or in dependency of an already determined movement pattern or a movement characteristic, is provided. Optical outputting hereby preferably means the figurative representation of correction-, standard- and/or ideal-movements on a screen or a projection surface, wherein it is conceivable, that figurative outputting can be understood as representation of single images and/or an animated movie representation. Acoustic outputting hereby preferably describes the outputting of specific tones and/or the outputting of language statements. Haptic outputting can be understood e.g. as defined outputting of vibrations. In particular with respect to the optical outputting the correction-, standard-, and/or ideal-movements beside, over and/or in correlation to the actually recorded movement patterns or to the actually recorded movement characteristics are preferably outputable. Correction movements can hereby e.g. display an advise for movement amendments respectively adjustments with respect to the recorded movement pattern. Standard movements can be e.g. the average movements of a defined group of persons or those movements known from clinical studies. Ideal movements can be e.g. movements which are very gently, cleaning and/or time-efficient, etc.

According to a further preferred embodiment of the present invention a method for monitoring of monitoring dental treatment movements and for outputting correction parameters for adapting the dental treatment movements is provided. The method comprises the method for at least partially determining a movement pattern of a dental treatment means, in particular of a toothbrush, resulting from a dental treatment, in particular tooth cleaning, with the steps: Moving the dental treatment means for treatment of surface parts of the teeth at least in a X-/Y-plane, wherein by means of a preferably optical detection device, in particular a sensor device, data with respect to at least a movement parameter of the dental treatment means, in particular the movement direction or rotation, the acceleration, the path and/or the speed, are recorded, and providing of the recorded data to a processor device or a system for determination of the movement pattern and the steps of deriving or determining of correction parameters, in particular at least one movement direction, for adapting the movement of the dental treatment means as a function of the compared movement patterns, and outputting information by means of an outputting device as a function of the derived or determined correction parameters.

This method is advantageous, since a feedback respectively correction information with respect to the movement sequence is outputted to a person performing a dental treatment, in particular a tooth cleaning, respectively to a person performing a dental treatment are, in particular in real time, correction information for correction respectively adjustment of the movement sequence outputable, should the dental treatment means be guided with a movement assessed, in particularly by means of software, as being inappropriate or a movement pattern being assessed as inappropriate.

This embodiment is beneficial since e.g. children can be taught, in particular supervised, motion sequences with respect to dental treatment, in particular tooth cleaning, which are identified as being appropriate movement pattern. An optical outputting device, like e.g. a screen of a mobile phone, a watch, a bracelet, a game console or a tablet pc, can output an image or a video that visually shows respectively outputs the preferably optimal movement pattern, in particular movement patterns provided in a local storage means and/or on a server and/or in a local or internet based database in form of data, to the child. By means of an optical detection device or optical capturing device, in particular a camera, which is preferably coupled via signal with the outputting device and which is preferably arranged in the same housing as the outputting device, the motions of the child are detectable and thus supervisable. In case the child deviates from the displayed motions respectively movement patterns, then a signal is preferably outputable which elucidates the deviation to the child. The detection device and the outputting device, in particular for visual and/or haptic and/or acoustic outputting of signals and/or commands, are preferably components of a single apparatus, in particular a mobile apparatus. The apparatus is hereby preferably formed as portable processor device, in particular as mobile phone or tablet pc.

According to a further preferred embodiment of the present invention a registration of the teeth to be treated preferably takes place, wherein the registration comprises the optical recording by means of the detection device or a manual recording by means of an input mask, wherein the number and/or the location and/or the orientation and/or defects of at least individual teeth are recorded, and wherein the derivation or determination of the correction parameters preferably takes place taking account of the registered teeth. Hereby the input mask can be e.g. visualized by a display means of an end-user device, in particular of the end-user device which also comprises the detection device. By means of a input device, which can be a component of the display means, it can preferably be indicated from a person which number of teeth is present and/or which location and/or which direction and/or which defects single, multiple or all teeth have.

The derivation or determination of the correction parameters preferably takes place under taking into account of the registered teeth. Hereby, the registration of the teeth can be carried out e.g. by means of the, in particular optical, detection device, in particular a camera, that means that preferably at least one image of the dentition is captured, wherein the image is analyzed by means of software and e.g.

the number, direction and/or location and/or defects of the teeth are captured. Thus, it is also possible to capture tooth spaces of the dentition.

Additionally or as an alternative it is conceivable that the number, direction and/or location and/or defects of the teeth are capturable manually, in particular by means of an input mask. Additionally or alternatively the angle feature and/or sealings and/or dental crowns and/or inlays respectively filings of a single or of multiple teeth are capturable, in particular by means of the optical detection device. The location of the teeth preferably describes the position of the teeth respectively which tooth is the particular tooth (e.g. incisors, canine, premolars, molars). Furthermore, it is conceivable that properties of the individual teeth or relations between the individual teeth are capturable.

As defects are preferably understood gum recession and/or discolorations and/or dental calculus and/or cracks and/or breakages and/or holes and/or dental calculus etc.

Furthermore, it is preferably conceivable that a singular or repeated respectively multiple calibration step takes place. As calibration is hereby preferably understood the determination of concrete respectively personal properties of the body, in particular height or the distance of the head to the detection device or a reference point respectively the height or the distance of a part of the head to the detection device or to a reference point. Particular preferable multiple body-fixed points respectively surface points are captured by the optical detection device, wherein preferably one or multiple anterior teeth and/or the contact region extending in the tooth length direction respectively boundary region between the anterior teeth extending is captured. It is hereby preferably concerning the central incisor teeth, in particular of the upper jaw, wherein it is also conceivable that also or alternatively the central incisor teeth of the lower jaw are captured. The detection of the position of the incisor teeth of the upper jaw and/or the boundary region between those incisor teeth is often possible by pulled up lip, however this can be always ensured during tooth brushing. Nevertheless the detection of the position of the incisor teeth and/or the boundary region between the incisor teeth in relation to further anthropometric points of the face surface, in particular of the nose, cheeks and forehead region, wrinkles, in particular forehead wrinkles, or pupils, provides a possibility for the definition of a highly precise coordinate system respectively reference system at the head of a person. With respect to clinical studies, this should respectively can be put in relation preferably with established dental coordinate definitions like e.g. the Frankfurter horizontal plan; the camperschen plane, or the occlusal plane. Furthermore a coordinate system defined that way additionally can be coupled to exactly or at least one, two, three further body points or to multiple body points, in particular the nose, the chin, the forehead, one ear or two ears, etc. This is beneficial since on the one hand the once defined coordinate system is always detectable independently of the position of the lips, whereby the position of the teeth is always known, and on the other hand the shape of the body part, e.g. the nose, is irrelevant. The eventually occurring soft part deformation during mouth opening should respectively can be compensated by means of correction computation to further raise the accuracy of the method.

According to a further preferred embodiment of the present invention the optical recording of an object takes place, wherein at least the extension of the object in one dimension, that means in length and/or in width and/or in height and/or circumference, is known and the extension of the object in the known dimension respectively in the known dimensions is preferably used for the determination of dimension parameters, to capture geometric relations, like e.g. the length of the path travelled by the dental treatment means during dental treatment and/or the dimension of the teeth, in particular of the visible parts of the teeth, etc. The object is hereby preferably the person, which is using the dental treatment means, wherein the known dimension of the person is preferably the height. Additionally or alternatively it is conceivable, that the object is the dental treatment means, in particular the tooth brush, wherein the known dimension of the toothbrush is preferably the length and/or the width and/or the height and/or the circumference.

Additionally or alternatively it is conceivable that the object is an element, which dimensions are substantially everywhere on earth identical, like e.g. a CD, DVD or credit card. Preferably is data with respect to the properties of the dental treatment means recordable by means of a identification means (cf. later embodiments).

Further it is conceivable that in or at the dental treatment means or a sensor device, in particular a pressure sensor, for bringing in contact with the dental treatment means for detecting the contract pressure applied by means of the dental treatment means to the mouth respectively the teeth and/or the gum is provided. Alternatively or additionally it is conceivable that the pressure detection is caused by means of the optical detection device. Wherein a bending of the dental treatment means is captured and placed in dependency of known strength values. The strength values can be hereby stored or storageable in a data base. Furthermore, it is conceivable that the dental treatment means is directly identified or the packaging thereof (e.g. a bar code or QR-code) is optically recorded and identified. The identification of the dental treatment means enables thereby, that the information belonging to a concrete dental treatment means with respect to its properties, in particular the strength values, are automatically stored for a processor device or are retrieved. Furthermore it is conceivable, that the information with respect the properties of the dental treatment means are also provideable respectively recordable respectively registerable also manually in a data base, in particular of a mobile end-user device. Preferable the information with respect to the property are in form of data storable locally on the mobile end-user device or on a server. Thus, according to a further preferred embodiment of the present invention a determination of pressure during tooth cleaning, in particular tooth brushing, applied by means of a dental treatment means, in particular a toothbrush, to the teeth or gum of the person performing the tooth cleaning, wherein an optical detection of the dental treatment means, in particular directly or indirectly, takes place by means of the optical detection device, wherein by means of the detection device image information are captured respectively image data is generated and by means of the image information respectively the image data a, in particular elastic, deformation, in particular bending, of the dental treatment means is determined, wherein the pressure is at least determined in dependency of the deformation of the dental treatment means and preferably further data, comprising properties of the dental treatment means. Furthermore, it is conceivable that a signal or information is outputable via an output device in dependency of the determined pressure. Preferably the signal or information represents a guidance for the user of the dental treatment means, in particular for the person having the dental treatment. The determination of the pressure respectively the output of the signals and/or information detected in dependency of the pressure takes place in real time. The output of the signals and/or information particular preferably takes place by means of an optical outputting device. The optical outputting device is preferably a component of the device, in particular of the end-user device, to which also belongs the optical detection device. The signals and/or information with respect to pressure are particular preferably communicated simultaneously and/or via the same outputting device to the same person by means of which the correction parameters for adapting the dental treatment motions are also communicated to a person, in particular the person having and/or performing the dental treatment. The data belonging to the properties of the dental treatment means can be material properties and/or strength values and/or dimensions and/or bending stiffness and/or brand and/or age and/or the number of usages, in particular operating life, etc.

According to a further preferred embodiment of the present invention can preferably by means of the optical detection device for determination of the reference system moving with the head of the treated person at least three preferably predetermined points, in particular surface points, of a body, in particular of a head, of a person, in particular with respect to which the movement patterns are recorded, are recorded, wherein at least two points are connectable respectively virtually connectable respectively imaginarily connectable with one line and at least a third point does not lie on said line, wherein the reference system is defined due to the at least three recorded points and wherein a movement of the dental treatment means is recorded with respect to this reference system or wherein by means of the optical detection device at least three preferably predetermined pointes of the hand guiding the dental treatment means, in particular a tooth brush, are recorded, wherein at least two points are connectable with one line and at least a third point does not lie on said line, wherein the reference system is defined due to the at least three recorded points and wherein a movement of the person, in particular of the head, is recorded with respect to this further reference system.

According to a further preferred embodiment of the present invention are recorded in dependency of a movement of the body, in particular of the head, of a person with respect to which the movement patterns are recorded, with respect to the optical detection device body-fixed surface points differing from each other, in particular of the head, of the person for the definition of the reference system. This embodiment is beneficial since the head of the person does not have to be fully motionless during execution of the method, but can preferably move and nevertheless a precise detection of the movement pattern is possible. Should e.g. a captured surface point not be capturable any more as a result of a head rotation of the person a further body fixed respectively head fixed point respectively surface point or multiple body fixed respectively head fixed points respectively surface points by means of which the reference system can be further maintained are preferably captured already before said surface point is not capturable anymore. As body fixed or head fixed points respectively surface points can be captured e.g. beside characteristic shapes, like e.g. the tip of the nose, color changes of the skin, in particular pigment disorder, pigmented nevus, scars, body jewelry, in particular tattoos, the cavity of the eye, the incisor teeth, in particular of the upper jaw, also points of devices arranged at the body, in particular at the head, like e.g. clothes, beanie, glasses.

According to a further preferred embodiment of the present invention the processor device is a mobile end-user device (e.g. a mobile phone or tablet pc), that sends the recorded data via the internet to a server device for further processing and/or receives data via the internet for outputting by means of an outputting means, wherein the data comprises information with respect to motion parameters of the dental treatment means. Furthermore, the before mentioned object is solved by a system for at least partially respectively at least partially indirect determination of a personal and preferably dynamic movement pattern of a dental treatment means, in particular a tooth brush, resulting from a dental treatment. A dynamic movement pattern is hereby preferably understood as a movement pattern, which is at least partially defined by velocity information and/or acceleration information of the dental treatment means with respect to a treatment area. The system preferably comprises at least one detection device, in particular a sensor device or an optical detection device for recording of data with respect to at least one movement parameter, in particular the movement direction, the acceleration, the traveled path and/or the velocity, of the dental treatment means and at least or exactly one data processing device for generating of movement patterns on the basis of the recorded data. It is hereby conceivable that the data processing device is a preferably with the internet at least timewise connectable device, in particular a computer, a digital camera, a gaming console, a tablet pc, a laptop, a wristwatch (e.g. a smart watch), a television and/or a mobile phone. Furthermore, it is conceivable that the data processing device generates the movement patterns partially or fully. Particular preferable transmits the data processing device the fully or partially generated movement patterns to a server device, which preferably receives personal movement patterns of dental treatment means from a plurality of data processing devices. The data transmission can take place e.g. in dependency of an energy-, connection-, time-, data volume- and/or dental-treatment-repeating-criteria, wherein the dental-treatment-repeating-criteria preferably states a concrete number of dental treatments. The connection criteria preferably states the type and/or source of the internet connection, e.g. if it is a mobile phone tariff or a local network, like e.g. a WLAN. The energy criteria preferably states the state of charge of an end-user devise powered, in particular with electricity, by means of a accumulator. This criteria dependent transmission of the partially or fully generated movement patterns is beneficial, since the computation of the movement patterns primarily takes place on the side of the data processing device, that means on the end-user device side, and thus the amount of data transfer between the individual end-user devices and the server device can be kept relatively small. This is further beneficial since the server device needs to have a significant smaller computing power in case it receives partially or fully prepared movement patterns and can process those. The server device preferably does not have to start with causing respectively computing the fully generation of movement patterns from the data. However, it is alternatively also conceivable that the data recorded by the detection device are transmitted for processing to the server device. Thereby, transmitting can take place immediately after the recording or in dependency of specific criteria. Hereby the criteria can be e.g. an energy-, connection-, time-, data volume-, and/or dental-treatment-repeating-criteria. The server device can be considered in this situation as data processing device for causing a processing of recorded data, that means on the end-user side respectively in the area of the detection device a data processing device is not necessarily required. Nevertheless, a processor device, in particular a mobile phone, is provided that at least causes the transmission of data to the server device. The server device has in a particular preferred embodiment access to clinically gathered information with respect to the dental health status, the number of dental visits per year and/or the treatment history, the used dental treatment means, etc. of concrete persons and connects these information with the recorded movement pattern of the respective person using that device. The recorded movement patterns of a concrete person are preferably by means of a personalization instance, like e.g. a name request, a password request, a phone number, an email address or a pseudonymous assignable to the concrete person. This embodiment is beneficial, since by means of the data consisting of the dental treatment status, the number of dental visits per year and/or the treatment history and the recorded movement parameters respectively the movement patterns generated by the server device obvious monitoring and supervision are performable and teachings for further enhancement of the dental treatment technique are exploitable.

A preferably in the system according to the invention employed respectively utilized dental treatment means, in particular a toothbrush, oral douche, gas transmitter, in particular air emitter, sand emitter, driller, ultrasonic cleaner, etc. preferably comprises at least one physical structure, wherein a treatment device for at least indirect binging into contact with a tooth surface and a contact region for holding the dental treatment means is arranged or attached at the physical structure, wherein a detection device, in particular a position-, velocity-, acceleration—and/or rotation sensor, for detection of movement parameters is at least during a usage of the dental treatment means physically connected with the physical structure. It is hereby conceivable that the detection device is coupled respectively coupleable with any dental treatment means. Furthermore, it is conceivable that the detection device is fix respectively permanent coupled with the electric toothbrush. According to a further preferred embodiment of the present invention the dental treatment means comprises a communication interface for transmitting the recorded data, in particular in raw state or in processed state, to a data processing device, wherein the communication interface is particular preferable designed in such a way that the data is transmittable wirelessly.

According to a further preferred embodiment of the present invention the system comprises a processor device, in particular a mobile end-user device, like e.g. a mobile phone, that preferably comprises at least one optical detection device, in particular a camera, for detecting data of at least one motion parameter, in particular the movement direction or—rotation, the acceleration, the traveled path and/or the velocity of a dental treatment means and a data processing device for the in particular image separation of the dental treatment means from at least one further recorded image component recorded by the optical detection device and for the determination of at least one movement pattern corresponding to the motion parameter.

The optical detection device is preferably used in the system as detection device for the at least partially determination of a personal movement pattern resulting from a dental treatment, in particular dental cleaning.

In case of a detection device, which is preferably designed as optical detection device or optical capturing device, it is conceivable that the dental treatment means is provided with characteristic optical shape, which preferably corresponds with an axis of abscissas respectively performs its functionality to further enable a three-dimensional recording of one concrete motion parameter of the dental treatment means during usage of exactly or at least one camera. However, it is also conceivable additionally or alternatively that the dental treatment means is equipped with one or multiple sensor devices and the data processing device uses for the determination of the motion parameters the sensor data and the data of the optical detection device.

Furthermore, it is also conceivable that the dental treatment means is equipped with one or multiple sensor devices, in case the processor device or the system comprises at least or exactly one, two or multiple cameras, in particular 3 cameras. In this case the data processing device can utilize data of single or multiple or all cameras and/or sensors for the determination of the motion parameters.

According to a further preferred embodiment of the present invention the optical detection device comprises at least one, in particular exactly or at least two, cameras for three-dimensional recording of the at least one motion parameter of a dental treatment means, wherein the processor device defines a three-dimensional coordinate system respectively reference system that moves during a movement of the dental treatment means with the dental treatment means together in space. Hereby the coordinate respectively reference system can be constituted by characteristic anthropometric body points, body lines and/or body surfaces of a body part of a person, in particular the hand, which is guiding the dental treatment means. However it can be also constituted additionally by means of surface points, -lines and/or -surfaces of the dental treatment means. The second camera is hereby preferably fixed arranged in relation the first camera, so that an once-only calibration of the detection system can take place before utilization. It is preferably also conceivable that the at least two cameras are moveable with respect to each other. The at least two cameras are preferably at least, exactly or as a maximum 2, 3, 4, 5 or 6 cameras.

According to a further preferred embodiment of the present invention the optical detection device records a part of the head respectively at least three points of the surface of the head respectively three body-fixed points, which move during a movement of the person, in particular the head, together with the person, in particular the head, and define a three-dimensional coordinate system respectively reference system in the recorded part of the head respectively by means of these points, wherein a movement of the dental treatment means is determined in dependency of the defined coordinate system of the head or a movement of the recorded part of the head is determined in dependency of the coordinate system of the dental treatment means. It is hereby conceivable that the coordinate system is directly associated with the dental treatment means, wherein it is additionally or alternatively also conceivable that the coordinate system is at least partially and preferably fully defined by means of defined body surface parts, in particular two or more knuckles of the hand constituting the linkage between the palm of the hand and the fingers.

This embodiment is beneficial since at least by means of the recording of the hand movement a movement of any dental treatment means is optically at least indirectly at least partially detectable and optical detection devices, in particular hand cameras, are very wide spread, whereby the invention is applicable for an extremely large number of persons. Particular preferably the dental treatment means is identifiable and separable from the remaining image parts by the data processing device in such a way that its movements, in particular with respect to or relative to a reference respectively coordinate system fixed at a head or in the region of the head of the person, are recordable and particular preferable analyzable. Furthermore, preferably at least or exactly one body part of a person is in particular additionally identifiable and separable by a data processing device from the remaining image parts in such a manner, that a motion parameter of the dental treatment means is determinable respectively computable with respect to the body part. The body part is preferably a part of the head, like e.g. forehead, eyebrows, eye hole, mouth, lips, ears, cheeks and/or chin, preferably one or multiple body-fixed, in particular cranium fixed, parts, like e.g. forehead, chin and/or nose. However, it is also conceivable that multiple body parts, like e.g. the eyes, the mouth and/or nose are recorded. It is thus conceivable that one or multiple photos of the user respectively the patient, in particular from the head respectively the face of the user, are recorded and stored. Individual body forms, in particular face-part-forms respectively forms of characteristic face features, are preferably manually or automatically recordable or definable respectively are registerable as reference points or reference surfaces with respect to which one or multiple motion parameters of the dental treatment means are recorded. As reference point can be used respectively registered hereby e.g. one or two eyes, the nose, the mouth, one or two ears and/or one or two lips. Furthermore, additionally or alternatively the eye brows or the eyes, in particular the pupils, of a person can be recorded. One line or axis can be defined respectively set connecting the eyes respectively the pupils, in particular the centers of the eyes respectively pupils. This line or axis can define a direction, in particular the x-, y- or z-direction, of a coordinate system. Furthermore, a second line or axis can be defined respectively set in the direction of extension of the nose, in particular of the nasal bridge, of that person which preferably defines a second direction differing from the first direction, in particular the x-, y- or z-direction, of the coordinate system. Preferably the first direction and the second direction are substantially or exactly aligned orthogonally. A third direction preferably extends orthogonally with respect to a plane set up by the first and second direction. The recording of a movement of the dental treatment means with respect to coordinate system coupled with a movement of the head is extremely beneficial since the person carrying out the dental treatment can perform head- and/or body movements without causing the recording of the movement patterns to become unprecise or impossible.

Furthermore, the present invention is directed to an usage of a position-, velocity- and/or acceleration sensor or a video tracking system for the determination of a movement pattern of a dental treatment means resulting during a dental treatment.

The present invention is further directed to a method for at least partially determining of a pressure resulting during a dental treatment, in particular tooth cleaning, and applied by means of a dental treatment means to the teeth or the gum of a person having the dental treatment. The method preferably comprises at least the steps: Performing of a at least indirect and preferably direct optical detection of at least one part of the dental treatment means during a dental treatment by means of an optical detection device respectively performing an optical recording of the dental treatment means during the dental treatment by means of an optical detection device. It is hereby preferably conceivable, that in case of an indirect recording of the dental treatment means a position and/or orientation and/or alignment of the hand by means of which the dental treatment means is guided is recorded. An indirect recording of the dental treatment means preferably describes the real optical recording of the dental treatment means. Generating of image data representing the optical recording, wherein the image data preferably comprises respectively represents several grades of deformation of the dental treatment means. As a deformation preferably a bending and/or torsion of a tooth brush shaft and/or of a tooth brush head is recorded. However it is additionally or alternatively also conceivable that a deformation of the bristles of a toothbrush is recorded respectively determined. Analyzing the image data for determining the respective grades of deformation of the dental treatment means. Determining of the pressure, wherein the pressure is at least determined in dependency of a deformation of the dental treatment means and in dependency of further dental treatment means data, wherein the dental treatment means data comprises data with respect to properties of the dental treatment means.

Furthermore, it is conceivable that in dependency of the determined pressure a signal or information is outputtable via an output device. Preferably represents the signal or the information a guidance for the user of the dental treatment means, in particular for the person having the dental treatment. The determination of the pressure respectively the output of the pressure detected in dependency of the signals and/or information to be outputted preferably takes place in real time. Outputting of the signals and/or information particular preferably takes place by means of an optical outputting device. The optical outputting device is preferably a component of a device to which also the optical detection device belongs. The signals and/or information with respect to the pressure are particular preferably simultaneously and/or by means of the same outputting device communicated to the same person, which is also used to communicate correction parameters for adapting the dental treatment movements of a person, in particular the person which has and/or performs the dental treatment. The data with respect to the properties of the dental treatment means can be material properties and/or strength values and/or dimensions and/or bending stiffness and/or brand and/or age and/or number of usage, in particular duration of usage, etc.

According to a further preferred embodiment of the present invention the optical recording of an object takes place, wherein at least the extension of the object in one dimension, that means length and/or width and/or height and/or circumference, is known and the extension of the object in the known dimension respectively in the known dimensions is used for the determination of dimension parameters to detect geometric relationships, like e.g. the length of the path traveled by the dental treatment means during dental treatment and/or the dimensions of the teeth, in particular of the visible parts of the teeth and/or the dimensions of the dental treatment means and/or the distance of the teeth and/or the dental treatment means with respect to the detection device, etc. The object is hereby preferably the person using the dental treatment means, wherein the known dimension of the person preferably is its height. It is additionally or alternatively conceivable that the object is the dental treatment means, in particular the toothbrush, wherein the known dimension of the toothbrush is preferably the length and/or width and/or height and/or circumference.

Furthermore, the present invention can refer to a system or a method comprising at least an optical detection device, in particular at least one camera, for recording of data with respect to at least one motion parameter, in particular the movement direction, the acceleration, the travelled path and/or the velocity, of a dental treatment means and a data processing device for separation of an image part representing the dental treatment means from at least one further image part recorded by the optical detection device and for determining of at least one movement pattern corresponding to the motion parameter by means of the separated image parts, wherein the optical detection device comprises preferably at least one camera, in particular exactly or at least two cameras, for the preferably three-dimensional recording of the at least one motion parameter of a dental treatment means, wherein the processor device preferably defines a three-dimensional coordinate system moving together in space with the hand guiding the dental treatment means during a movement of the dental treatment means, wherein the optical detection device preferably records a part of the head of a person and defines a three-dimensional coordinate system at the recorded part of the head, wherein a movement of the dental treatment means is preferably determined in dependency of the defined coordinate system of the head or wherein a movement of recorded part of the head is determined in dependency of the coordinate system of the dental treatment means, wherein the processor device is preferably a mobile phone or a tablet pc and sends the recorded data preferably by means of the internet to a server device for further processing and/or receives via internet data for outputting by means of a outputting device of the mobile phone or the tablet pc, wherein the data preferably comprise information with respect to motion parameters of the dental treatment means and/or the pressure, with which the dental treatment means is pressed against the teeth and/or the gum.

A data base is preferably provided comprising dental-treatment-means-data. It is hereby conceivable that the data base is provided locally on the end-user device and/or on a server. An identification means, in particular a software based identification means, is preferably provided. The identification means records e.g. optically the dental treatment means or the dental treatment means represents information, like e.g. a QR-code. The optically recorded dental treatment means is preferably represented by means of image information respectively image data, which are preferably correlated with image information respectively image data with respect to a plurality of dental treatment means provided in said data base. In the data base are preferably data respectively information with respect to properties of the individual dental treatment means provided. In case of a match of the data respectively information provided in the data base with the image data respectively image information recorded preferably a selection and utilization of the data respectively information provided in the data base with respect to the concrete respectively identified dental treatment means for determining the pressure takes place. A link with the data respectively information, which are provided in the data base, associated with a dental treatment means is further possible by means of a linkage, like e.g. by means of reading out a code, in particular an optical code, like e.g. a bar code or QR-code. Furthermore, it is additionally or alternatively conceivable that a screen for manually inputting of the dental-treatment-means-data respectively—properties is provided and the manually inputted data respectively information are used for determining the pressure. Additionally or alternatively is conceivable that by means of a radio device, like e.g. a near-field-communication (NFC) or by means of Bluetooth, the data respectively information with respect to a dental treatment means are transferred into the data base or a linkage to the data base is generated or the data for determining the pressure are stored.

The invention further refers to a computer program product for executing of one or multiple previously mentioned methods and/or for statistical analysis of the generated datasets. The terms optical detection device and optical capturing device can be understood as synonym in the context of this invention.

Further benefits, goals and features of the present invention will be described by the following specification of the attached figures, in which exemplarily features according to the invention, processor devices or systems for recording the movement patterns during a dental treatment are illustrated. Components of the devices and methods according to the inventions, which match at least essentially with respect to their function can be marked with the same reference sign, wherein such components do not have to be marked or described in all figures.

In the following the invention is just exemplarily described with respect to the attached figures.

Figure 1B:
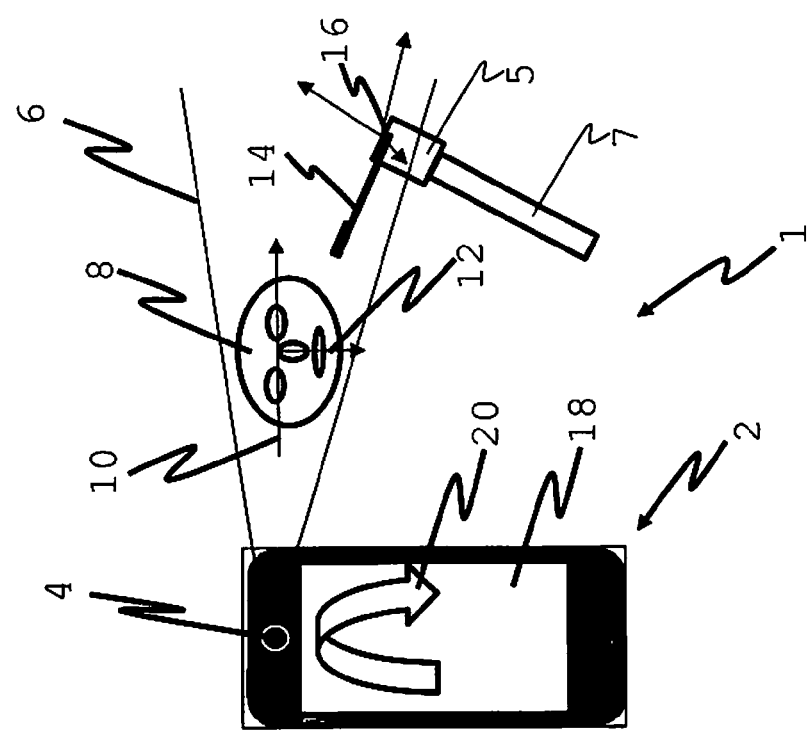
Figures 2A, 2B:
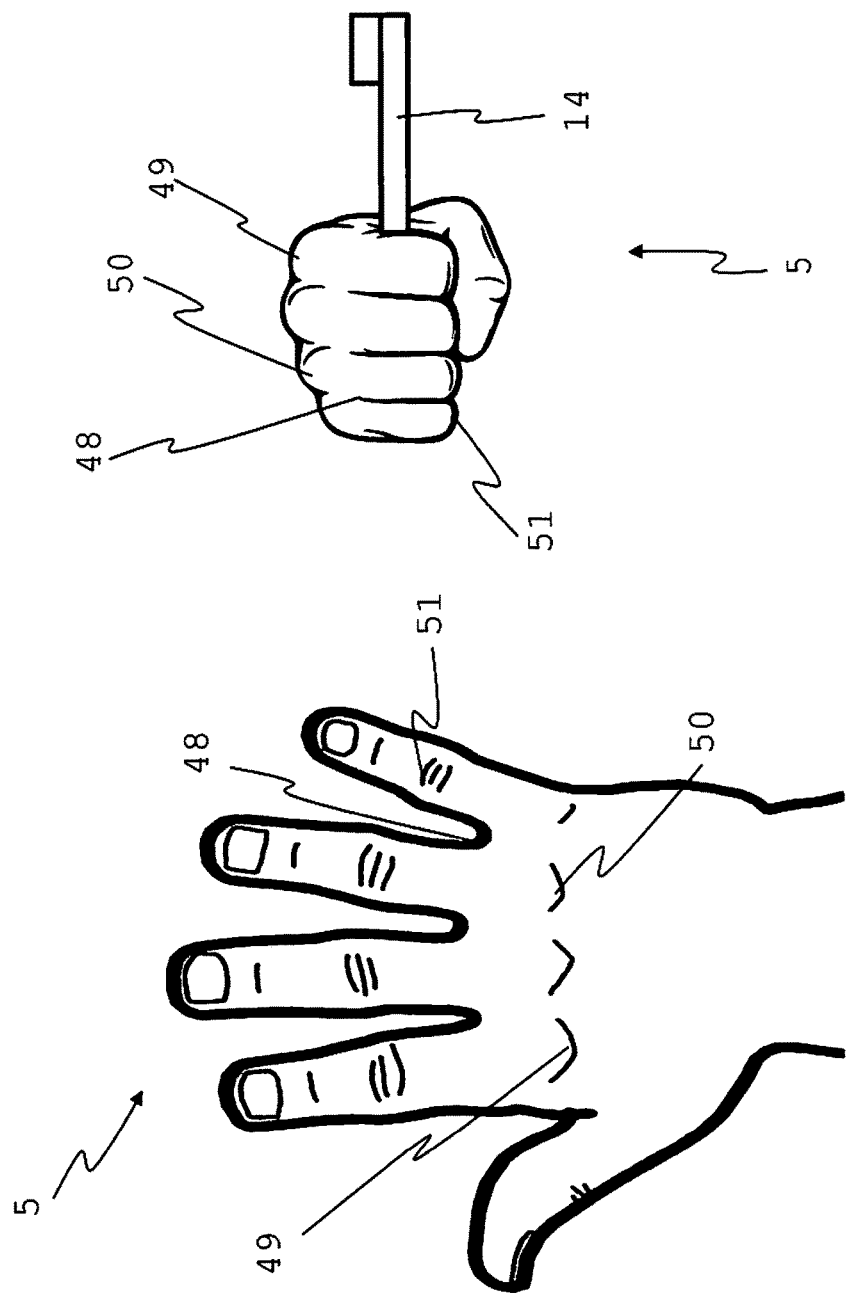

Therein shows:

FIG. 1a a system according to the invention for recording of dental treatment movements;

FIG. 1b an internet based network according to the invention, in which multiple systems according to the invention are involved;

FIG. 2a an outstretched hand with characteristic surface points or surface parts; and FIG. 2b a hand clenched to a first with characteristic surface points or surface parts, holding a dental treatment means.

In FIG. 1a a system 1 for recording of dental treatment movements by means of a processor device 2 respectively a mobile end-user device 2 is shown. The mobile end-user device 2 which is preferably a mobile phone, hereby preferably has at least or exactly one optical detection device 4, in particular an optical capturing device 4, that can be preferably formed as a camera. Hereby, the camera preferably records exactly or more than 15 fps (frames per second), exactly, up to or more than 30 fps, exactly, up to or more than 45 fps, exactly, up to or more than 60 fps, exactly, up to or more than 75 fps, exactly, up to or more than 90 fps, exactly, up to or more than 120 fps or exactly, up to or more than 200 fps. Reference number 6 characterizes the recording area, in which preferably at least one part of the head, in particular one or both pupils, the nose and/or the mouth, of a person 8 as well as at least one part of the hand 5 guiding the dental treatment means 14 is present. Reference numbers 10 and 12 are characterizing preferably person-fixed axes respectively coordinate means, which follow a movement of the head preferably exactly. Reference number 14 characterizes a dental treatment means being formed as toothbrush, which is according to reference number 16 moved in space and thus with respect to the head. With the optical outputting device 18 of the processor device 2 motion sequences for correcting of the movement and/or for the definition of a motion sequence are displayable.

FIG. 1b shows that multiple processor devices 2 transmit via a data link, in particular an internet link, data to a server, that preferably generates optimized movement characteristics, in particular in dependency of medical condition histories or defect histories of the individual persons.

Both FIGS. 1a and 1b underlie the method according to the present invention for determining of a movement pattern of a dental treatment means, in particular a toothbrush, resulting during a dental treatment, in particular dental cleaning. The method according to the present invention hereby at least comprises the steps:

Moving the dental treatment means for the treatment of surface parts of the teeth in at least a x-/y-plane, wherein by means of at least one optical detection device 4 data with respect to at least one motion parameter, in particular the movement direction or –rotation, the acceleration, the path and/or the velocity, of the dental treatment means 14 is recorded with respect to a reference system 10 moving with the head 8 of the treated person. The data preferably consist of image information, like e.g. arrangement of pixels, and preferably describe at least one part of the head 8 of the person and one part of the hand 5 of the person, with which the person is guiding the dental treatment means. Reference number 7 characterizes the arm of the person from which the hand 5 guiding the dental treatment means 14 extends.

The processor device 2 defines a further three-dimensional reference system 16, that moves during a movement of the dental treatment means 14 in space together with the dental treatment means 14, wherein the further reference system 16 is particular preferably defined by characteristic anthropometric body points of the hand, body lines of the hand and/or body surfaces of the hand, with which the dental treatment means 14 is guided. This is beneficial since the dental treatment means 14 is fully enclosed by the hand 5 of the user and thus can be at least partially invisible for the optical detection device 4. Based on the movement of the characteristic, in particular anthropometric, body points of the hand, body lines of the hand and/or body surfaces of the hand defining the further reference system 16 the position and/or orientation of the dental treatment means 14 is determinable. The processor device 2 analyzes for the definition of the further three-dimensional reference system 16 preferably data, in particular image information, recorded by the optical detection device 4.

However, it is also conceivable that the data recorded by the optical detection device 4 are processed respectively analyzed by means of a processor device 2, which is formed outside the mobile end-user device. Hereby is preferably conceivable that the processor device is a server device receiving the date via an internet connection. The processor device formed as server device preferably sends the processed or modified or analyzed data or data based thereon via an internet connection to the end-user device.

Providing the recorded data to that or to a further processor device for the determination of the movement pattern as well as preferably the determination of the movement pattern by means of the processor device or by means of the further processor device. It is hereby conceivable the further reference system is defined e.g. by means of a processor device of a mobile or stationary end-user device. Hereby preferably data recorded by means of the optical detection device 4 with respect to the reference system 10 moving with the head 8 of the person and with the respect to the reference system 10 moving with the hand 5 of the person is analyzed. Particular preferably the relative movements of the reference systems 10, 16 are determined with respect to each other.

Further, preferably at least timewise, in particular before and/or during tooth brushing, the orientation and/or position of the dental treatment means 14, in particular of the bristle part of the toothbrush, is determined with respect to the hand 5 guiding the dental treatment means 14. The determination of the position and/or orientation of the dental treatment means 14, in particular the bristle part of the toothbrush, preferably takes place by means of an analysis of the data determined by the optical detection device 4.

FIG. 2a shows the back of the hand 5, wherein the reference numbers 48, 49, 50 and 51 characterize only exemplarily characteristic points on the surface of the hand. Thus, reference number 48 characterizes the transition between two fingers. Reference numbers 49 and 50 characterize the knuckles of the hand and reference number 51 characterizes a knuckle of a finger. It was recognized that the body surface points respectively—parts and similar body surface points respectively—parts are always very characteristic and are therefore very useful for an optical recording, whereby the present invention enables a very simple and functionally very reliable method for a user.

In FIG. 2b the hand 5 is only exemplarily shown together with a dental treatment means 14. This illustration shows individual characteristic body points respectively—sections, as they are preferably recorded by the optical detection device 4.

The invention claimed is:

1. A method comprising:
positioning a tablet pc or mobile phone such that a camera of the tablet pc or the mobile phone views a head and a hand of a person,
moving an electric toothbrush held by the hand relative to teeth of the person in order to treat surface portions of the teeth,
causing the camera to record video image data that includes: (i) a first set of data that includes at least a part of the head or at least three points on a surface of the head that move during movement of the head while treating the teeth, and (ii) a second set of data relating to acceleration or rotation of the electric toothbrush relative to a first three-dimensional reference system, wherein the second set of data represent characteristic body points of the hand, body lines of the hand and/or body surfaces of the hand that is moving the electric toothbrush,
providing the recorded video image data to a processor device of the tablet pc or mobile phone,
using the processor device of the tablet pc or mobile phone to define the first three-dimensional reference system based upon the first set of data,
using the processor device to define a second three-dimensional reference system which at least at times during the movement of the electric toothbrush moves in space with the electric toothbrush, wherein the second three-dimensional reference system is defined based upon the recorded second set of data,
determining at least one relative movement between the first three-dimensional reference system and the second three-dimensional reference system,
determining correction movements based on the determined at least one relative movement, and
optically outputting correction information on a screen of the mobile phone or tablet PC based on the determined correction movements.

2. A method comprising:
moving a toothbrush at least in an X-/Y-plane to treat surface parts of teeth of a person,
using a camera of a tablet PC or mobile phone to capture more than 15 frames per second of an image area containing one or both pupils, the nose, eyebrows, eye hole, lips, ears, cheeks and/or chin of the person,
recording sensor data with respect to rotation movements or acceleration movements of the toothbrush using an acceleration sensor or a rotation sensor, respectively, disposed in the toothbrush,
processing the recorded sensor data in the toothbrush,
wirelessly communicating the processed data via a communication interface of the toothbrush to the mobile phone or tablet PC,
comparing the processed data with movement patterns or movement characteristics stored in a database of the mobile phone or tablet PC,
determining correction parameters for adapting the movement of the toothbrush based on the compared movement patterns,
generating an animated representation based on the determined correction parameters, and displaying the animated representation on a screen of the mobile phone or tablet PC.

3. The method according to claim 2, wherein the toothbrush comprises an outputting device for haptic and/or acoustic outputting of signals and/or commands.

4. The method according to claim 3, wherein the mobile phone or tablet PC transmits raw or processed movement pattern data to a server and the server device sends processed or modified or analyzed data via an internet connection to the mobile phone or tablet PC.

5. The method according to claim 4, wherein the recorded movement patterns of the person are linked by a personalization instance to the person which is brushing teeth.

6. The method according to claim 5, wherein a pressure sensor for detecting the contact pressure between the toothbrush and the teeth is provided.

7. A method comprising:
moving a toothbrush at least in an X-/Y-plane to treat surface parts of teeth of a person,
using a camera of a tablet PC or mobile phone to capture more than 15 frames per second of an image area containing one or both pupils, the nose, eyebrows, eye hole, lips, ears, cheeks and/or chin of the person, as well as the moving toothbrush, thereby generating image data,
recording sensor data with respect to rotation movements or acceleration movements of the toothbrush using an acceleration sensor or a rotation sensor, respectively, disposed in the toothbrush,
processing the recorded sensor data in the toothbrush,
wirelessly communicating the recorded and processed sensor data via a communication interface of the toothbrush to the mobile phone or tablet PC,
using a data processing device of the mobile phone or the tablet PC to identify the toothbrush in the image data based upon the shape of the toothbrush and to separate toothbrush data from the remaining image parts of said image data in such a way that movements of the toothbrush are analyzable,
using the data processing device to identify at least one body part of the person in the image data and to separate body part data from the remaining image parts of said image data,
using the data processing device to determine a motion parameter of the identified toothbrush with respect to the identified body part,
comparing the recorded sensor data and the generated image data with movement patterns or movement characteristics stored in a database,
determining correction parameters for adapting the movement of the toothbrush based on the compared movement patterns, and
optically outputting correction information on a screen of the mobile phone or tablet PC based on the determined correction parameters.

8. The method according to claim 7, wherein a registration of the teeth to be treated takes place, wherein the determination of the correction parameters takes place taking into account the registered teeth.

9. The method according to claim 8, wherein the toothbrush comprises an outputting device for haptic and/or acoustic outputting of signals and/or commands.

10. The method according to claim 9, wherein the mobile phone or tablet PC transmits raw or processed movement pattern data to a server or wherein the server device sends processed or modified or analyzed data via an internet connection to the mobile phone or tablet PC.

11. The method according to claim 10, wherein the recorded movement patterns of the person are linked by a personalization instance to the person which is brushing teeth.

12. The method according to claim 11, wherein a pressure sensor for detecting the contact pressure between the toothbrush and the teeth is provided.

13. The method according to claim 7,
wherein the screen outputs an animated representation of the captured scene, and
wherein the animated representation is generated as function of the determined correction parameters.

14. A method for monitoring of dental treatment movements of a person brushing teeth and for outputting correction parameters for adapting the dental treatment movements, comprising:
moving a toothbrush at least in an X-/Y-plane to treat surface parts of teeth of a person, the toothbrush comprising a brush head for contacting a tooth surface and a contact region for holding the toothbrush,
using at least one sensor device of a detection device that is non-permanently attached to the toothbrush to record rotation movements or acceleration movements of the toothbrush and generate recorded sensor data, wherein the sensor device comprises an acceleration sensor or a rotation sensor, respectively, the detection device comprising an outputting device for visual or haptic or acoustic outputting of signals or commands,
processing the recorded sensor data in the detection device,
wirelessly communicating the processed sensor data via a communication interface of the detection device to a mobile phone or tablet PC,
comparing the processed sensor data with movement patterns or movement characteristics stored in a database,
determining correction parameters for adapting the movement of the toothbrush based on the compared movement patterns, and
optically outputting information on a screen of the mobile phone or tablet PC based on the determined correction parameters.

15. The method according to claim 14, wherein the mobile phone or tablet PC transmits raw or processed movement pattern data to a server or wherein the server device sends processed or modified or analyzed data via an internet connection to the mobile phone or tablet PC.

16. The method according to claim 15, wherein the recorded movement patterns of the person are linked by a personalization instance to the person which is brushing teeth.

17. The method according to claim 16, further comprising:
using a camera of the tablet PC or mobile phone to capture more than 15 frames per second of an image area containing one or both pupils, the nose, eyebrows, eye hole, lips, ears, cheeks and/or chin of the person, thereby generating image data, and
displaying an animated representation of the captured image area on the screen of the mobile phone or tablet PC,
wherein the animated representation is generated as function of the determined correction parameters.

* * * * *